(12) United States Patent
Beckstead et al.

(10) Patent No.: US 8,553,210 B2
(45) Date of Patent: Oct. 8, 2013

(54) SYSTEM AND METHOD FOR COMBINED RAMAN AND LIBS DETECTION WITH TARGETING

(75) Inventors: Jeffrey Beckstead, Valencia, PA (US); Patrick Treado, Pittsburgh, PA (US); Matthew Nelson, Harrison City, PA (US)

(73) Assignee: ChemImage Corporation, Pittsburgh, PA (US)

( * ) Notice: Subject to any disclaimer, the term of this patent is extended or adjusted under 35 U.S.C. 154(b) by 74 days.

(21) Appl. No.: 13/209,688

(22) Filed: Aug. 15, 2011

(65) Prior Publication Data

US 2012/0038908 A1   Feb. 16, 2012

Related U.S. Application Data

(63) Continuation-in-part of application No. 11/656,393, filed on Jan. 23, 2007, now Pat. No. 7,999,928, and a continuation-in-part of application No. 12/899,055, filed on Oct. 6, 2010, and a continuation-in-part of application No. 12/899,119, filed on Oct. 6, 2010, and a continuation-in-part of application No. 12/199,145, filed on Aug. 27, 2008, now Pat. No. 8,054,454.

(51) Int. Cl.
*G01N 21/00*   (2006.01)

(52) U.S. Cl.
USPC ............. 356/73.1; 356/73; 356/446; 356/301

(58) Field of Classification Search
USPC .................. 356/73, 73.1, 445, 446, 451, 301
See application file for complete search history.

(56) References Cited

U.S. PATENT DOCUMENTS

| | | |
|---|---|---|
| 4,880,052 A | 11/1989 | Meyer |
| 5,194,912 A | 3/1993 | Batchelder |
| 5,377,004 A | 12/1994 | Owen |
| 5,442,438 A | 8/1995 | Batchelder |
| 5,528,393 A | 6/1996 | Sharp |
| 5,539,517 A | 7/1996 | Cabib |
| 5,623,345 A | 4/1997 | Merchant et al. |
| 5,689,333 A | 11/1997 | Batchelder |

(Continued)

FOREIGN PATENT DOCUMENTS

JP     9121889     5/1997

OTHER PUBLICATIONS

Caetano et al., "Evaluation of the Importance of Non-Linear Spectral Mixing in Coniferous Forests," SPIE vol. 3499, Sep. 1998, pp. 257-269.

(Continued)

*Primary Examiner* — Gregory J Toatley
*Assistant Examiner* — Iyabo S Alli

(57) ABSTRACT

A system and method for locating and identifying unknown samples. A targeting mode may be utilized to scan regions of interest for potential unknown materials. This targeting mode may interrogate regions of interest using SWIR and/or fluorescence spectroscopic and imaging techniques. Unknown samples detected in regions of interest may be further interrogated using a combination of Raman and LIBS techniques to identify the unknown samples. Structured illumination may be used to interrogate an unknown sample. Data sets generated during interrogation may be compared to a reference database comprising a plurality of reference data sets, each associated with a known material. The system and method may be used to identify a variety of materials including: biological, chemical, explosive, hazardous, concealment, and non-hazardous materials.

17 Claims, 9 Drawing Sheets

(56) References Cited

U.S. PATENT DOCUMENTS

| | | | |
|---|---|---|---|
| 5,710,626 | A | 1/1998 | O'Rourke |
| 5,862,273 | A | 1/1999 | Pelletier |
| 5,866,430 | A | 2/1999 | Grow |
| 5,901,261 | A | 5/1999 | Wach |
| 5,911,017 | A | 6/1999 | Wach |
| 6,002,476 | A | 12/1999 | Treado |
| RE36,529 | E | 1/2000 | Lewis |
| 6,717,668 | B2 | 4/2004 | Treado |
| 6,954,667 | B2 | 10/2005 | Treado |
| 6,965,793 | B2 | 11/2005 | Treado |
| 6,992,809 | B1 | 1/2006 | Wang |
| 7,161,672 | B2 * | 1/2007 | Gornushkin et al. ......... 356/328 |
| 7,362,489 | B2 | 4/2008 | Wang |
| 7,474,685 | B2 | 1/2009 | Kalayeh |
| 7,542,138 | B2 * | 6/2009 | Gardner, Jr. ................. 356/301 |
| 7,692,775 | B2 | 4/2010 | Treado |
| 2008/0088837 | A1 | 4/2008 | Gardner |
| 2009/0128802 | A1 | 5/2009 | Treado |

OTHER PUBLICATIONS

Rasmussen et al., "Library Retrieval of Infrared Spectra Based on Detailed Intensity Information," Applied Spectroscopy, vol. 33, No. 4, Feb. 1979, pp. 371-376.

Guilment et al., "Infrared Chemical Micro-Imaging Assisted by Interactive Self-Modeling Multivariate Analysis," Applied Spectroscopy, vol. 48, No. 3, 1994, pp. 320-326.

Malinowski, :Factor Analysis in Chemistry, 1991, 2nd Edition, Published by John Wiley and Sons, Inc. William H. Press, et al, pp. 208-265.

Marquardt, et al, "Novel Probe for Laser-Induced Breakdown Spectroscopy and Raman Measurements Using an Imaging Optical Filter," Applied Spectroscopy, 1998. p. 1146-1153, vol. 52, No. 9.

Wiens et al., "Development of a Prototype Laser-Induced Breakdown Spectroscopy (LIBS) Instrument with Standoff Distances," Spectrochimica Acta Part A vol. 61, issue 10, Aug. 2005, p. 2324-2334.

Thompson et al., Combined Remote LIBS and Raman Spectroscopy Measurements. Lunar and Planetary Science Conference, XXXVI, #1517, Houston, Texas, Mar. 14-18, 2005, (*available at : http://www.lpi.ursa.edu/meetings/lpsc2005/pdf/1517.pdf), last accessed Sep. 23, 2008.

Hubble et al., A Combined Remote LIBS and Raman Spectroscopy Study of Minerals, Lunar and Planetary Science Conference, XXXIII, #1935, Houston, Texas, Mar. 11-15, 2002. (Available at: http:www.lpi.usra.edu/meetings/ipsc2002/pdf/1935.pdf), last accessed Sep. 23, 2008.

Wiens, et al, "Joint Analysis by Laser-Induced Breakdown Spectroscopy (LIBS) and Raman Spectroscopy at Standoff Systems," Spectrochimica Acta Part A 61 (2005) 232-2334.

* cited by examiner

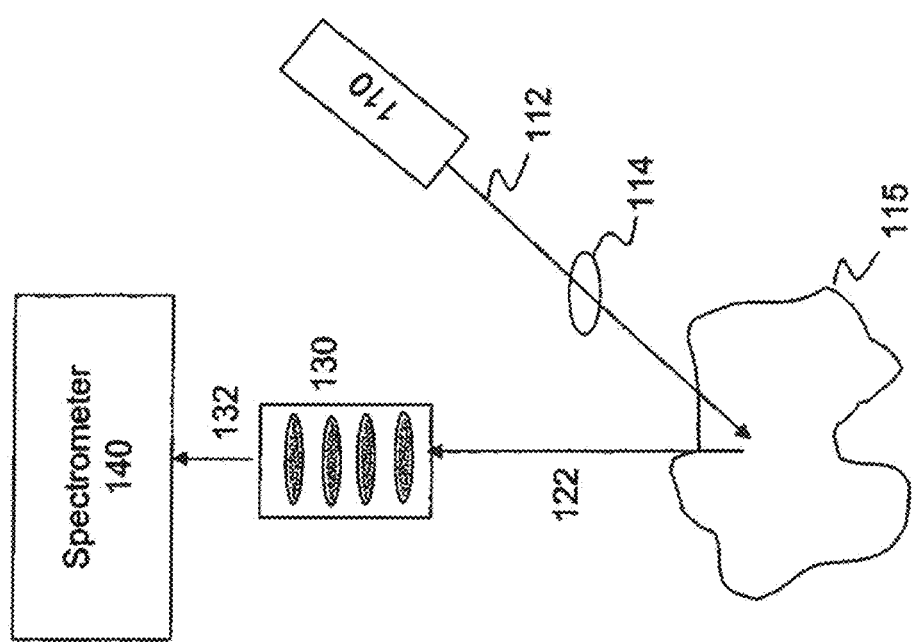

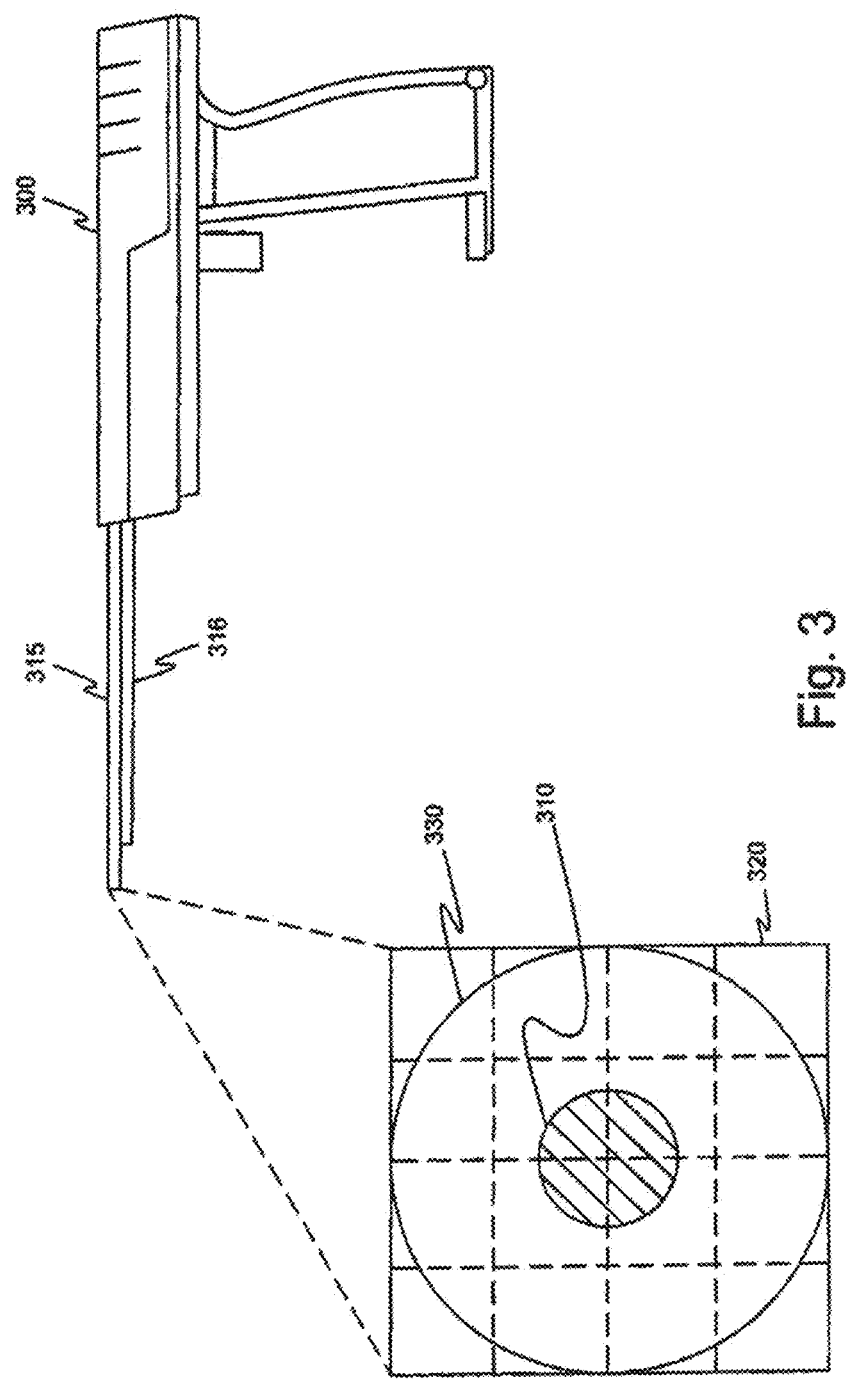

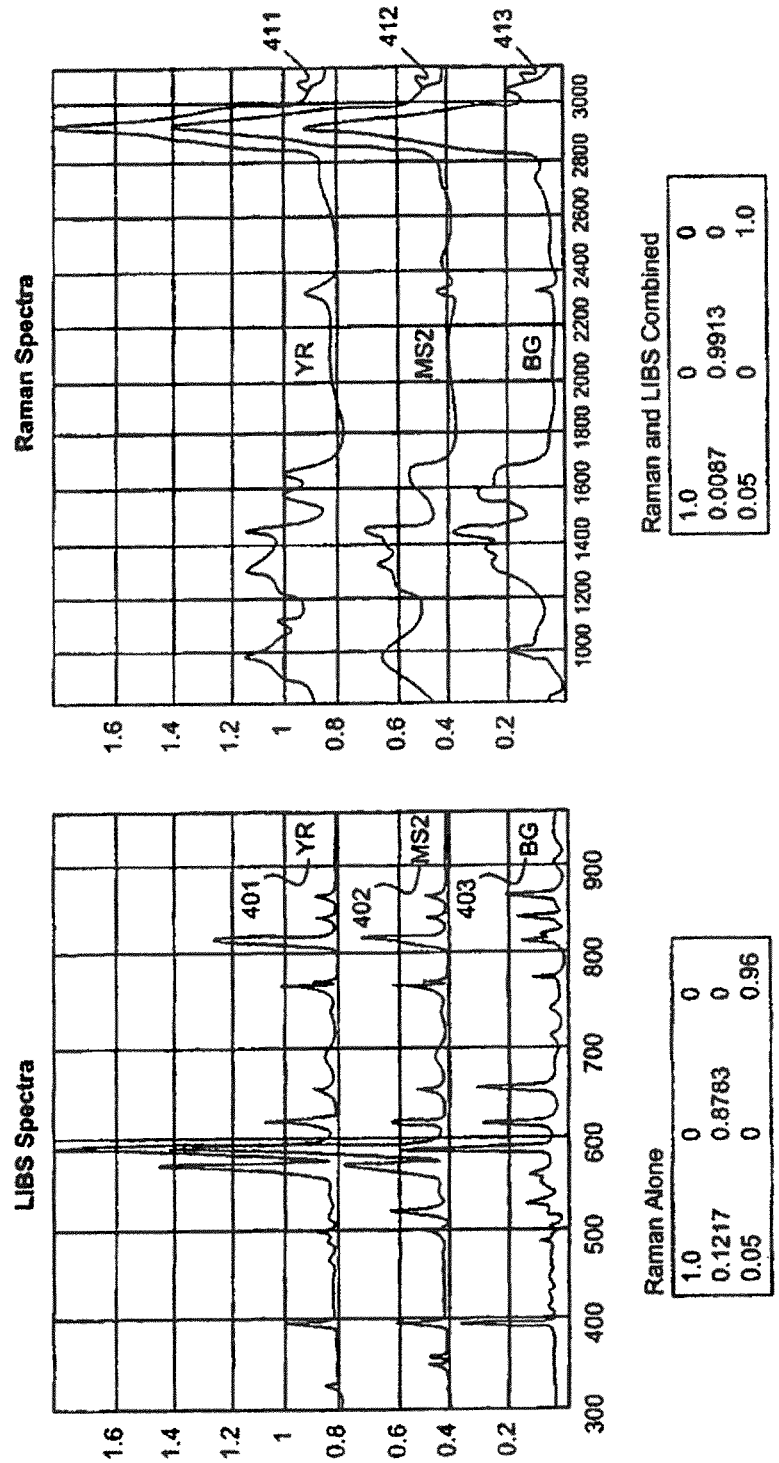

SYSTEM AND METHOD FOR COMBINED RAMAN AND LIBS DETECTION WITH TARGETING

RELATED APPLICATIONS

This Application is a continuation-in-part of pending U.S. patent application Ser. No. 11/656,393, filed on Jan. 23, 2007, entitled "Method and System for Combined Raman and LIBS Detection," which itself claims priority under 36 USC §119(e) to the following provisional patent applications No. 60/761,235, filed on Jan. 23, 2006, entitled "Combined Raman And LIBS Biochem Detection System"; No. 60/761,256, filed on Jan. 23, 2006, entitled "Raman Detection Of Waterborne Threats"; and No. 60/761,235, filed on Jan. 23, 2006, entitled "Combined Raman And LIBS Biochem Detection System."

This Application is also a continuation-in-part of pending U.S. patent application Ser. No. 12/899,055, filed on Oct. 6, 2010, entitled "System And Method For Combined Raman And LIBS Detection," which itself is a continuation-in-part of pending U.S. patent application Ser. No. 11/656,393, filed on Jan. 23, 2007, entitled "Method and System for Combined Raman and LIBS Detection." application Ser. No. 12/899,055 also claims priority to Provisional Patent Application No. 61/278,393, filed on Oct. 6, 2009, entitled "Use Of Magnification To Increase SWIR HSI Detection Sensitivity."

This Application is also a continuation-in-part of pending U.S. patent application Ser. No. 12/899,119, filed on Oct. 6, 2010, entitled "System and Method for Combined Raman, SWIR and LIBS Detection," which itself is a continuation in part of U.S. patent application Ser. No. 12/199,145, filed on Aug. 27, 2008, entitled, "Time And Space Resolved Standoff Hyperspectral IED Explosives LIDAR Detector" and claims priority under §119(e) to the following U.S. Provisional Patent Applications No. 61/403,141, filed on Sep. 10, 2010, entitled "Systems And Methods For Improving Imaging Technology"; No. 61/324,963, filed on Apr. 16, 2010, entitled "Short-Wavelength Infrared (SWIR) Multi-Conjugate Liquid Crystal Tunable Filter"; No. 61/305,667, filed on Feb. 18, 2010, entitled "System and Method for Detecting Explosives on Shoes and Clothing"; No. 61/301,814, filed on Feb. 5, 2010, entitled "System and Method for Detecting Hazardous Agents including Explosives"; No. 61/335,785, filed on Jan. 12, 2010, entitled; and No. 61/278,393, filed on Oct. 6, 2009, entitled "System and method for SWIR HSI for daytime and nighttime operations."

This Application is also a continuation-in-part of pending U.S. patent application Ser. No. 12/199,145, filed on Aug. 27, 2008, entitled "Time And Space Resolved Standoff Hyperspectral IED Explosives LIDAR Detector," which itself is a continuation of U.S. Pat. No. 7,692,775, filed on Jun. 9, 2006, entitled "Time And Space Resolved Standoff Hyperspectral IED Explosives LIDAR Detection", and claims priority under §119(e) to the following provisional patent applications No. 60/786,978, filed on Mar. 29, 2006, entitled "Time and Space Resolved Standoff Hyperspectral IED Explosives LIDAR Detection (TSR-SHIELD)"; and No. 60/699,251, filed on Jul. 14, 2005, entitled "SHIELD: Standoff Hyperspectral Imaging Explosives LIDAR Detector/Optical Standoff Detection Of Explosive Residue."

Each of the above-referenced patents and patents applications are hereby incorporated by reference in their entireties.

BACKGROUND

Deployment of threat agents poses significant risks to both human and economic health. The risk is compounded by a limited ability to detect the deployment of these agents. Prior art detection strategies rely on separate instrumentation for detection and identification of the threat agent. Conventional means to identify a threat agent include wet chemical methods or spectroscopic methods. Reagent-based identification of biological threat agents includes methods such as specific antibodies, genetic markers and propagation in culture. While highly specific, these identification methods are time-consuming, labor-intensive and costly.

Spectroscopic means, for identification, provide an alternative to reagent-based identification methods and include mass spectrometry, infrared spectroscopy, Raman spectroscopy, laser induced breakdown spectroscopy (LIBS), and imaging spectrometry. Mass spectrometry is limited by sensitivity to background interference. Infrared spectroscopy holds potential for quickly scanning a region of interest to identify unknown materials. Raman spectroscopy is a good candidate for detection of threat agents based on its ability to provide a molecular "fingerprint" for materials. With high specificity, Raman spectroscopy can be implemented in several different configurations, including normal Raman spectroscopy. UV resonance Raman spectroscopy, surface enhanced Raman spectroscopy (SERS) and non-linear Raman spectroscopy.

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the entire area encompassing the sample simultaneously using an electronically tunable optical imaging filter such as an acousto-optic tunable filter ("AOTF") or a LCTF. This may be referred to as "wide-field imaging". Here, the organic material in such optical filters are actively aligned by applied voltages to produce the desired bandpass and transmission function. The spectra obtained for each pixel of such an age thereby forms a complex data set referred to as a hyperspectral image ("HSI") which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet ("UV"), visible ("VIS"), near infrared ("NIR"), short-wave infrared ("SWIR"), mid infrared ("MIR") wavelengths and to some overlapping ranges. These correspond to wavelengths of about 180-380 nm (UV), 380-700 nm (VIS), 700-2500 nm (NIR), 900-1700 nm (SWIR), and 2500-25000 nm (MIR).

While normal Raman spectroscopy has demonstrated adequate sensitivity and specificity for detection of airborne matter, other forms of Raman spectroscopy suffer from inadequate sensitivity, specificity or signature robustness. LIBS is also a good candidate for detection of threat agents based on its ability provide an elemental "fingerprint" for materials with high sensitivity. Prior art imaging spectroscopy is limited by the need to switch from a broadband light source, for optical imaging, to a substantially monochromatic light source for spectroscopic imaging. This results in delay and inefficiency during detection during which the sample may degrade.

There exists a need for accurate and reliable detection of a variety of agents including but not limited to biological, chemical, explosive, hazardous, concealment, and non-hazardous. There exists a need for a system and method that can detect and unknown material in a region of interest and interrogate the unknown material to thereby identify it as a known material.

SUMMARY OF THE INVENTION

The present disclosure relates generally to the identification of unknown samples. More specifically the present disclosure relates to systems and methods for targeting and identifying an unknown sample in a region of interest. The system and method of the present disclosure also provide for operation in at least two modalities. First, the present disclosure contemplates a targeting mode, for scanning a region of interest to thereby identify an unknown sample. Short wave infrared (SWIR) and fluorescence techniques may be implemented in this targeting mode. The present disclosure then contemplates an identification mode, for interrogating and indentifying the unknown sample.

In order to improve the overall sensitivity and specificity of fieldable threat detection, the invention of the present disclosure combines two well known and proven techniques in this identification mode, Raman and laser induced breakdown spectroscopy (LIBS), into a system optimized for threat detection. Both individual methods have demonstrated the ability to detect threats in point sensing, proximity sensing and standoff sensing configurations. Improved overall detection performance can be realized through appropriate chemometric spectral processing algorithms applied to the fused data of the two orthogonal techniques. By combining Raman and LIBS techniques, threat detection performance can be improved relative to the individual techniques acting alone.

The present disclosure contemplates that the systems and methods disclosed herein may be use to identify materials including, but not limited to, biological materials, chemical materials, explosive materials, hazardous materials, concealment materials, non-hazardous materials, and combinations thereof. The system and method disclosed herein hold potential for application in a variety of configurations including standoff, on-the-move (OTM), stationary, portable, handheld, and combinations thereof.

BRIEF DESCRIPTION OF THE DRAWINGS

These and other embodiments of the disclosure will be discussed in relation to the following non-limiting and exemplary drawings, in which:

FIG. 1 is a spectroscopy system according to one embodiment of the disclosure;

FIG. 3 is a schematic representation for an apparatus according to one embodiment of the disclosure;

FIGS. 4A and 4B respectively show LIBS and Raman spectra of a sample; and

DETAILED DESCRIPTION

Figure 2A:
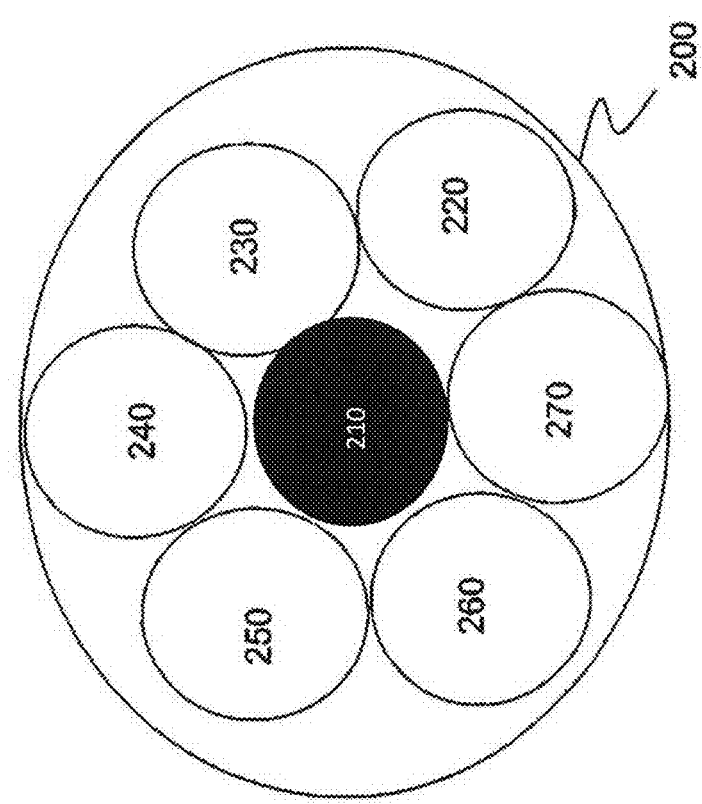
FIG. 2A is an exemplary structured illumination configuration according to one embodiment of the disclosure.

Raman spectroscopy has emerged as an attractive candidate for reagentless detection technology and shows significant capabilities in controlled studies for field detection of a variety of agents including: chemical, Radiological, nuclear, and explosive (CBRNE) biological agents. Specifically, Raman sensing may hold potential for detection of chemical surface contamination, on-the-move detection, white powder identification using handheld Raman sensors, and for waterborne pathogen detection.

Laser Induced Breakdown Spectroscopy (LIBS) is a type of atomic emission spectroscopy which uses a highly energetic laser pulse as the excitation source. Because all substances emit light when excited to sufficiently high temperatures, LIBS can detect all elements, limited only by the power of the laser as well as the sensitivity and wavelength range of the spectrograph and the detector. The development of the broadband, high-resolution spectrometer, along with advanced chemometric approaches, has enabled LIBS to demonstrate real-time detection and discrimination of hazardous chemical, biological and explosive (CBRNE) materials. Operationally, LIBS is very similar to arc/spark emission spectroscopy. The laser pulses delivered to the sample can be mildly destructive of the sample. However, the laser pulses can be directed to a specific region of the sample, making the surrounding sample material available for Raman sampling.

Thus, according to one embodiment of the disclosure an integrated detection system synergistically combines Raman detection mode with LIBS technologies to provide an integrated and efficient detection system. The combined Raman/LIBS sensory system can provide reagentless sensing technology for the detection and identification of chemical or biological agents. In another embodiment, the disclosure relates to a structured illumination method and apparatus.

FIG. 1 is a spectroscopy system according to one embodiment of the disclosure. The system shown in FIG. 1 can be configured as a handheld device, point detection device, or a standoff detector device. The spectroscopy device of FIG. 1 can be used, for example, to simultaneously obtain spectroscopic images of a sample. The images can define different spectroscopic modes such as laser scattering, ultraviolet laser induced fluorescence (UV-LIF) and laser induced breakdown spectroscopy (LIBS). In FIG. 1, illumination source 110 provides a plurality of illuminating photons to sample 115. Optical device 114 may include one or more light gathering optics and it may optionally be used to focus, filter or direct illumination photons 112 to sample 115. Once illuminated, sample photons 122 can be collected by gathering optics 130 and directed to spectrometer 140. Spectrometer 140 can be configured to receive and process different types of spectra simultaneously. In one embodiment, spectrometer 140 receives and processes sample photons for simultaneously forming Raman and LIBS spectra for sample 115. In one embodiment, first sample photons are processed to obtain Raman spectra for the sample and then second sample photons are processed to obtain LIDS spectra for the sample.

The exemplary system of FIG. 1 can include a fiber array spectral translator ("FAST"). The FAST system can provide faster real-time analysis for rapid detection, classification, identification, and visualization of, for example, explosive materials, hazardous agents, biological warfare agents, chemical warfare agents, and pathogenic microorganisms, as well as non-threatening objects, elements, and compounds. FAST technology can acquire a few to thousands of full spectral range, spatially resolved spectra simultaneously, This may be done by focusing a spectroscopic image onto a two-dimensional array of optical fibers that are drawn into a one-dimensional distal array with, for example, serpentine ordering. The one-dimensional fiber stack is coupled to an imaging spectrograph. Software may be used to extract the spectral/spatial information that is embedded in a single CCD image frame.

One of the fundamental advantages of this method over other spectroscopic methods is speed of analysis. A complete spectroscopic imaging data set can be acquired in the amount of time it takes to generate a single spectrum from a given material. FAST can be implemented with multiple detectors. Color-coded FAST spectroscopic images can be superimposed on other high-spatial resolution gray-scale images to provide significant insight into the morphology and chemistry of the sample.

The FAST system allows for massively parallel acquisition of full-spectral images. A FAST fiber bundle may feed optical information from is two-dimensional non-linear imaging end (which can be in any non-linear configuration, e.g., circular, square, rectangular, etc.) to its one-dimensional linear distal end. The distal end feeds the optical information into associated detector rows. The detector may be a CCD detector having a fixed number of rows with each row having a predetermined number of pixels. For example, in a 1024-width square detector, there will be 1024 pixels (related to, for example, 1024 spectral wavelengths) per each of the 1024 rows.

The construction of the FAST array requires knowledge of the position of each fiber at both the imaging end and the distal end of the array. Each fiber collects light from a fixed position in the two-dimensional array (imaging end) and transmits this light onto a fixed position on the detector (through that fiber's distal end).

Each fiber may span more than one detector row, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

In one embodiment, the portable device may comprise FAST technology available from ChemImage Corporation, Pittsburgh, Pa. This technology is more fully described in the following U.S. patents, hereby incorporated by reference in their entireties: U.S. Pat. No. 7,764,371, filed on Feb. 15, 2007, entitled "System And Method For Super Resolution Of A Sample In A Fiber Array Spectral Translator System"; U.S. Pat. No. 7,440,096, filed on Mar. 3, 2006, entitled "Method And Apparatus For Compact Spectrometer For Fiber Array Spectral Translator"; U.S. Pat. No. 7,474,395, filed on Feb. 13, 2007, entitled "System And Method For Image Reconstruction In A Fiber Array Spectral Translator System"; and U.S. Pat. No. 7,480,033, filed on Feb. 9, 2006, entitled "System And Method For The Deposition, Detection And Identification Of Threat Agents Using A Fiber Array Spectral Translator".

For example, transmission line 132 can comprise a fiber bundle such that a first end of the fiber bundle optically communicates with gathering optics 130 while the second end of the fiber bundle communicates with spectrometer 140. The first end of the fiber bundle can comprise a two dimensional non-linear array of fiber bundles. The second end of the fiber bundle can comprise a curvilinear array of fibers wherein curvilinear may include a straight line as well as a curved line configuration. In an alternative embodiment, the system of FIG. 1 may additionally include an optical filter such as Liquid Crystal Tunable Filter (LCTF), Multi-Conjugate Liquid Crystal Tunable Filter (MCF) or an Acousto-Optic Tunable Filter (AOTF). The system of FIG. 1 may also be configured for use with Computed Tomography Imaging Spectroscopy (CTIS).

FIG. 2A is an exemplary structured illumination configuration according to one embodiment of the disclosure. In FIG. 2A, illumination circle 200 represents an illuminated area of a sample. Area 200 can be illuminated with photons having a first wavelength and region 210 can be illuminated with photons having a second wavelength. Thus, area 200 can be illuminated with photons of a first wavelength to obtain a Raman spectra for area 200. Thereafter, region 210 can be illuminated with photons of a second wavelength to obtain LIBS spectra for region 210. The sample can be illuminated to obtain Raman spectra before LIBS. Alternatively, the sample can be illuminated to obtain LIBS spectra before Raman. In still another embodiment, the annulus area between rings 200 and 210 can be used to obtain LIBS spectra and region 210 can be used for obtaining Raman spectra.

In an embodiment, area 200 and region 210 can be illuminated simultaneously with photons of different wavelength. Photons of a first wavelength can illuminate the entire area 200 (or the annulus region between area 200 and region 210), and photons of a second wavelength can illuminate region 210. Raman spectra can be collected from regions 220-270, while LIBS spectra are simultaneously collected from region 210. In the event that the region 210 is illuminated simultaneously with photons of the first and second wavelength, optical filters and detectors can be used to remove unwanted sample photons.

In another embodiment of FIG. 2A, each of regions 220-270 shows a region of the sample from which Raman-scattered photons may be collected. Region 210 can represent region for which LIBS can be implemented to obtain an atomic signature of the sample under study. The atomic signature of the sample can define the chemical identify of the sample at region 210. Regions 210-270 can have the shape of a circle, an ellipse, a rectangle, a square, a hexagon or any other shape. The combined analysis is advantageous in that it provides a significant synergistic performance of Raman and LIBS. That is, the structured illumination provides the specificity of Raman molecular spectroscopy along with LIBS elemental spectroscopy.

The structured illumination configuration of FIG. 2A can reflect an arrangement of the illumination sources (not shown). For example, the illumination configuration can comprise a first laser source for illuminating the entire region with photons of a first frequency and a second laser source for illuminating region 210 with photons of a second frequency. The arrangement of the first and second laser sources can be adapted to provide the structured illumination of FIGS. 2A-2C or variations thereof.

As stated, area 200 and region 210 can be illuminated simultaneously or sequentially. In one embodiment, area 200 is first illuminated with photons of the first wavelength. Sample photons can then be collected from each of the regions 220-270. Next, region 210 can be illuminated with photons of a second wavelength and sample photons can be collected therefrom. In an embodiment where the first wavelength provides a Raman spectrum and the second wavelength provides laser induced breakdown spectroscopy of the sample, collecting Raman photons from the sample before implementing laser induced breakdown spectroscopy enables Raman detection before a region of the sample (e.g., region 210) may be partially destroyed by LIBS.

In another embodiment, area 200 is illuminated substantially simultaneously with region 210. That is, photons of the first wavelength and photons of the second wavelength are directed to the sample at substantially the same time to independently collect sample photons from area 200 and region 210. According to this embodiment, the detection and analysis of the sample can be implemented simultaneously. Such implementation can be particularly beneficial for large samples where a sample is divided into a number of segments and each segment is analyzed independently of the remaining segments.

Figure 2B:
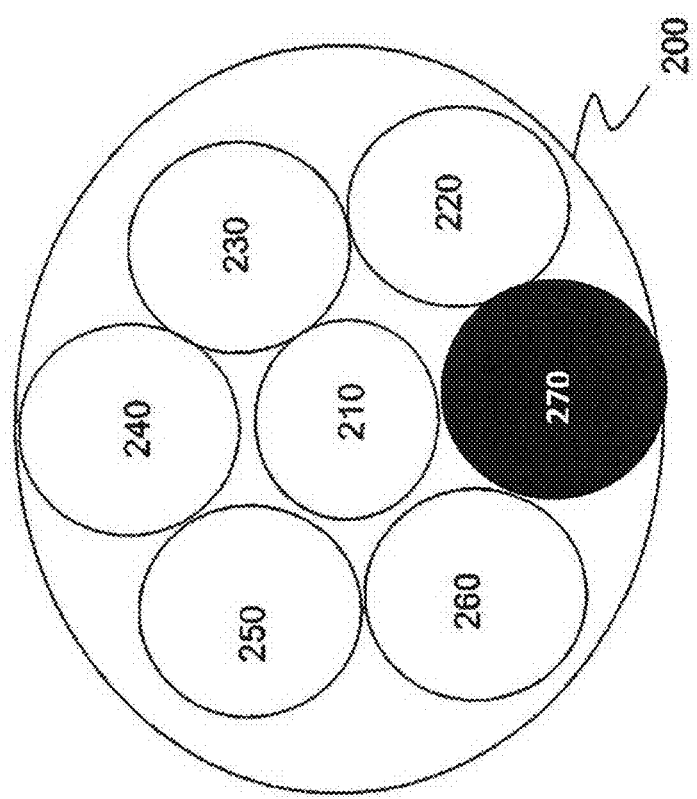
FIG. 2B is another exemplary structured illumination configuration according to one embodiment of the disclosure.

FIG. 2B is another exemplary structured illumination configuration according to an embodiment of the disclosure. In the structured illumination configuration of FIG. 2B, the area 200 is illuminated with photons of a first wavelength and region 270 can be illuminated with photons of a second wavelength. The photons of the first wavelength can elicit Raman spectra for regions 210-260 while sample photons collected from region 270 can identify the sample through LIBS. The illumination of area 200 and region 270 can overlap. That is, both area 200 and region 270 can be illuminated simultaneously.

Figure 2C:
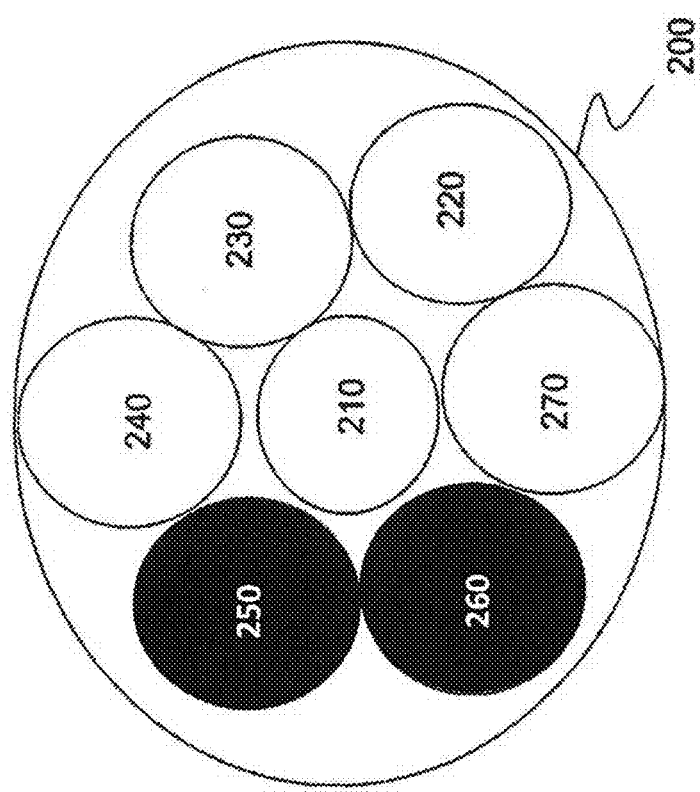
FIG. 2C is yet another exemplary structured illumination configuration according to one embodiment of the disclosure.

Similarly, FIG. 2C is yet another exemplary structured illumination configuration according to one embodiment of the disclosure. In FIG. 2C, area 200 is illuminated with photons having a first wavelength to collect sample photons from regions 210, 220, 230, 240 and 270. Photons having a second wavelength illuminate different regions of the sample to provide sample photons from regions 250 and 260. The sample photons from different regions 210-270 can be used to identify the sample. For example, if Raman spectra is collected from regions 210, 220, 230, 240 and 270 and regions 250 and 260 are used for LIBS, the sample under study can be identified by its Raman spectra and its atomic emission.

FIG. 3 is a schematic representation for an apparatus according to one embodiment of the disclosure. FIG. 3 can provide illumination source as well as the collection optics and the spectroscopy device. More specifically, FIG. 3 provides integrated handheld device 300 for sample detection and analysis. Handheld device 300 can include illumination source 315 and collection point 316. The illumination source can be integrated with the handheld device or it can be provided as a nozzle attachment. In one embodiment of the disclosure, nozzle 316 can be configured to collect sample photons. Further, the illumination source an be configured to provide structured illumination for sample 320. In FIG. 3, sample 320 is illuminated with photons of a first wavelength at region 310 and photons of a second wavelength at region 330. Regions 310 and 330 can overlap as shown. Photons collected from region 310 can provide laser induced breakdown spectroscopy and photons collected from the remainder of region 330 can be used to construct a Raman spectra for the sample. Both regions 310 and 330 of sample 320 can be illuminated simultaneously by an illumination source configured to provide photons of a first wavelength to region 330 and photons of a second wavelength to region 310. The illumination source may comprise two laser illumination devices concentrically positioned to form an annulus and to provide the illumination shown in FIG. 3.

FIG. 4A shows LIBS spectra collected from a sample. Specifically, FIG. 4A shows the presence of *Yersinia rhodei* (YR) 401, MS2 bacteriophage virus 402, and *bacillus globigii* (BG) 403 as indicated by each of their respective spectra. FIG. 4B shows Raman spectra collected from the sample of FIG. 4A. The Raman spectrum for each of YR 411, MS2 virus 412 and BG 413 are shown. In addition, at the bottom of FIGS. 4A and 4B, confusion matrices are shown for each of the Raman, LIBS and combined Raman/LIBS sensing, respectively, of YR, MS2 and BG.

A confusion matrix quantifies the degree or relatedness of spectra within specific classes contained in a training dataset, as well as providing an estimate of the degree of specificity inherent in the analysis and dominant sources of interference between classes (crosstalk). In this example, the classes are comprised of Yr, MS2 and BG. The confusion matrix is calculated by organizing the species-level Raman spectra into three unique classes. PCA analysis was performed and the first 10 PCs were employed to construct a supervised Mahalanobis distance model boundary classifier for each of the 3 biological classes. The classifier consisted of a mean spectrum, covariance matrix, and an ellipsoidal boundary. Each spectrum, as a point in the N=10 dimensional PC dataspace, was compared with the ellipsoidal boundaries. The minimum distance classification rule (nearest neighbor approach) was used whereby a spectrum was deemed a member of a particular class (ellipsoidal boundary) if its distance from that class was less than its distance from all other classes. Each row in the confusion matrix is the biological identity of the spectra, and the column entries show how the Mahalanobis distance based classifier classified the spectra. A perfect classifier has entries only along the diagonal. Confusion matrices are a predictor of the specificity of an identification algorithm in which the diagonal elements are correlated with the probabilities of correct identification ($P_d$) for each of the species, while the off-diagonal elements correlate with the probability of false positive ($P_{fp}$). The confusion matrix can change depending on the spectral range and number of principal components employed to construct the MD model. In the confusion matrices of FIGS. 4A and 4B, it is evident that there is a reduction in probability of false positive detections in the Raman/LIBS combined approach relative to Raman or LIBS operating alone.

Figure 5:
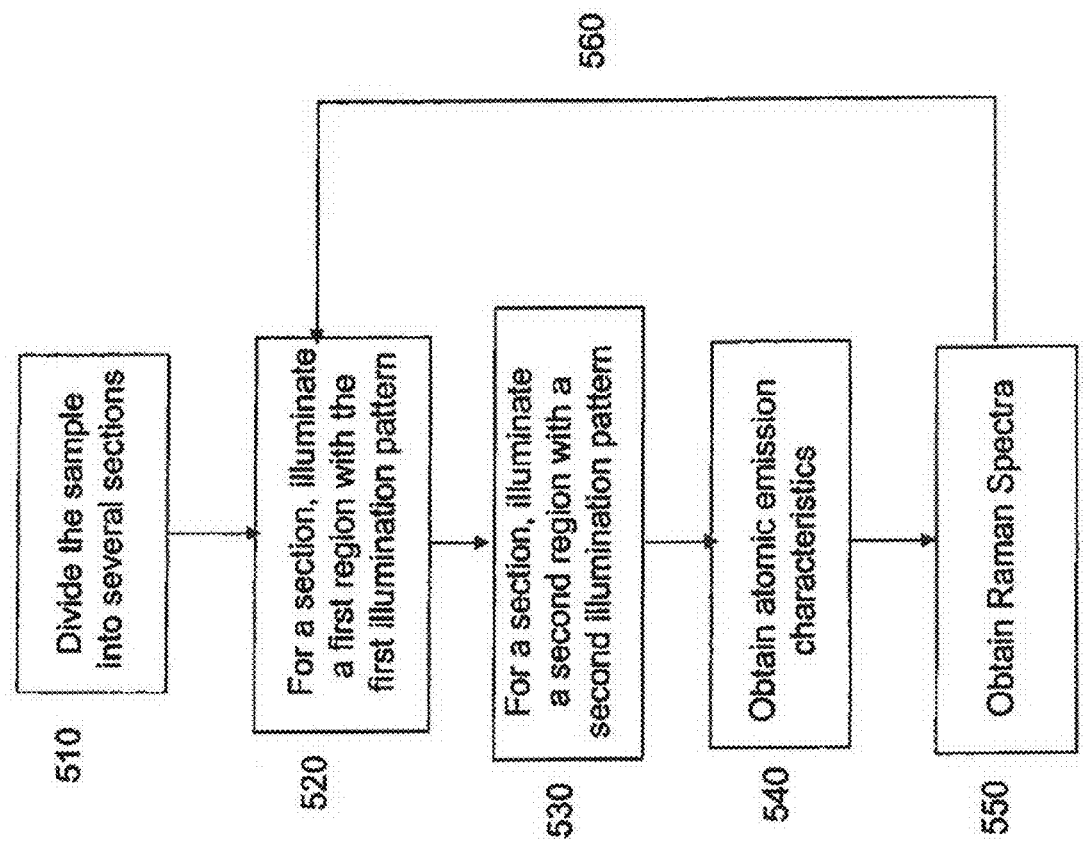
FIG. 5 is illustrative of a method of the present disclosure.

FIG. 5 is an exemplary algorithm according to an embodiment of the disclosure. The exemplary algorithm of FIG. 5 can define a software or a firmware. The exemplary algorithm of FIG. 5 can be used with the system of FIG. 1 or apparatus of FIG. 3. In the optional step 510, the sample is visually divided into several sections. For example, the sample can be visually divided into a grid and each grid (section) can be analyzed independently. In step 520, a selected section of the sample is illuminated with photons of a first wavelength to obtain a first sample photons. The first sample photons can be used for Raman spectroscopy. In step 530, the selected section is illuminated with photons of a second wavelength to obtain second sample photons. The second sample photons can be used for laser induced breakdown spectroscopy. Steps 520 and 530 can be implemented substantially simultaneously or sequentially.

The first sample photons can be used to obtain the Raman spectra for the sample at step 540. The information can also be used to obtain a spatially accurate, wavelength resolved image of the section under study. That is, the spatially accurate, wavelength resolved image of the sample can be obtained for the Raman spectra as well as the LIBS spectra. A spatially accurate wavelength-resolved image is an image of a sample that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (wave numbers) of interest. The second sample photons can be used to obtain the atomic characteristic of the sample in step 550. The results from steps 540 and 550 can be used to section of the sample under study. Steps 520-550 can be repeated to study different visual sections of the sample as shown by arrow 560.

In another embodiment, the disclosure relates to a method and apparatus for detecting and identifying chemical or biological agents, including aerosols and low vapor pressure chemicals by using electrostatic collection devices with hyperspectral Raman imaging devices. The detection processes can be implemented without using reagents. An exemplary system can include: (1) an electrostatic collector for particulate collection and low vapor pressure chemical aerosol collection; (2) an autonomous surface deposition subsystem providing concentrated threat agents; (3) a hyperspectral Raman imaging sensor optionally having a low-power imaging sensor, a digital camera for sample focusing and an imaging spectrometer for generating spatially-resolved Raman spectra with sampling statistics necessary to differentiate target from background; and (4) a decision making algorithm for threat agent identification in the presence of clutter or background noise.

In another embodiment, the disclosure relates to a reagentless detector for biological threats in water. Biological sample variables include: genetic near neighbors, strain, serotype, growth conditions and viability. To identify the substance, Mahalanobis Distance correlation metric can be used. In a method according to one embodiment, detection and identification of waterborne threats without using reagents comprises the following process steps: sample collection; agent pre-concentration; detection and identification; automated decision making; and data management. The agent pre-concentration step can include: sample collection, water-contaminant pre-concentration, and sample deposition. The detection and identification step can include optical microscopy as well as Raman spectroscopy and imaging. The automated decision making step may include one or more algorithm for analyzing the spectroscopy results and identifying the sample.

The present disclosure provides for a method for targeting and identifying an unknown material. One embodiment, the method, provides for scanning a region of interest to thereby identify an unknown sample. This "scanning" may be referred to as operating in a targeting mode. In one embodiment, this targeting mode may implement SWIR and/or fluorescence techniques to locate an unknown sample. This unknown sample may then be further interrogated using Raman and LIBS techniques to identify the unknown sample.

Figure 6:
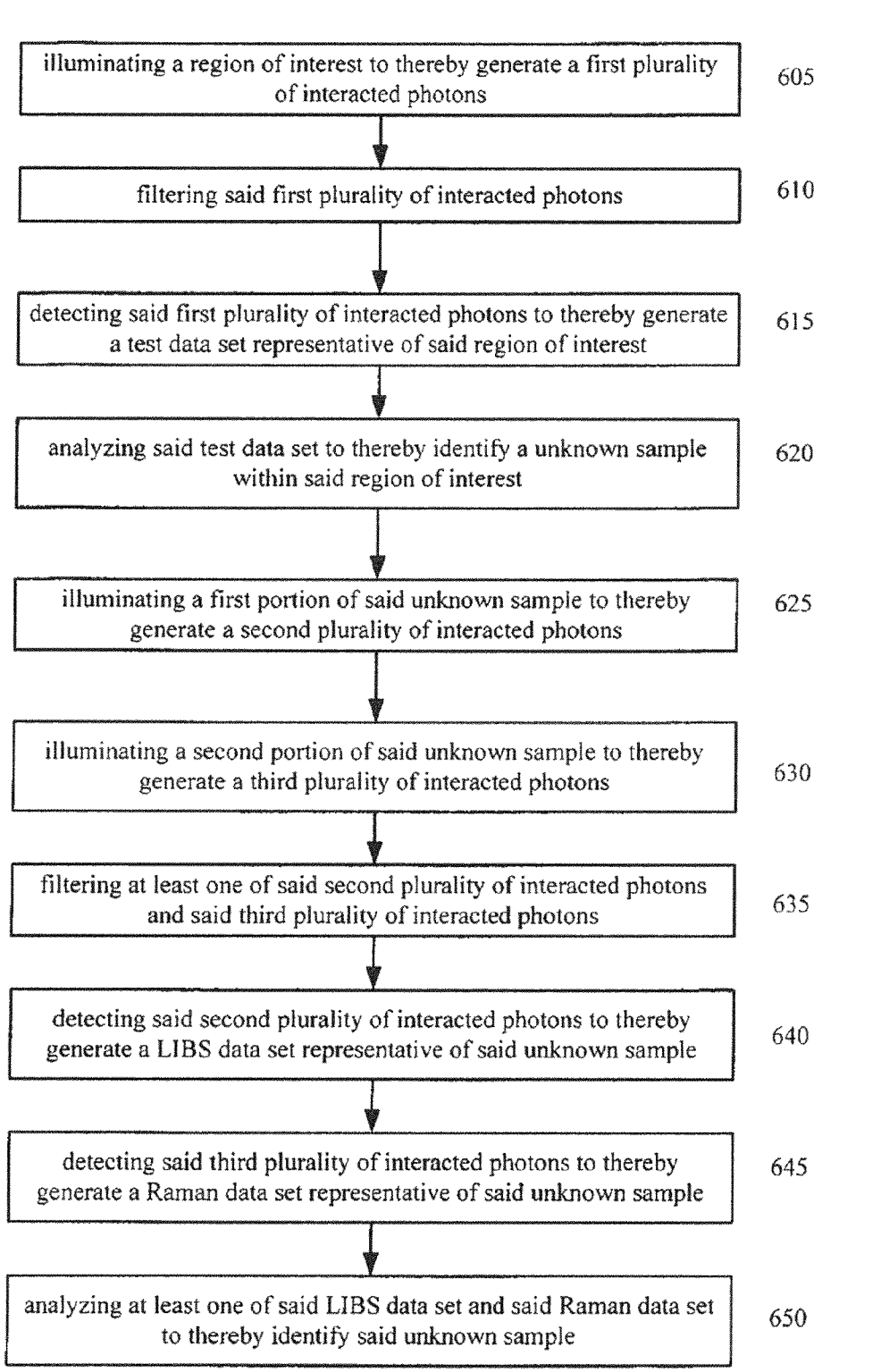
FIG. 6 is illustrative of a method of the present disclosure.

In one embodiment, illustrated by FIG. 6, the method 600 comprises illuminating a region of interest in step 605 to thereby generate a first plurality of interacted photons. Interacted photons as described herein may refer to one or more of the following: scattered photons, reflected photons, absorbed photons, luminescence emitted photons, plasma emitted photons, transmitted photons, and combinations thereof. Interacted photons may be generated by illuminating a region of interest and/or an unknown sample.

This illumination may be accomplished using active illumination, passive illumination, or combinations thereof. Active illumination may be accomplished by configuring an active illumination source to illuminate the region of interest. This active illumination source may comprise a laser light source, a broadband light source, an ambient light source, and combinations thereof. In one embodiment, a laser light source may comprise a tunable laser. In another embodiment, passive illumination may be accomplished by configuring a passive illumination source to illuminate the region of interest. This passive illumination source may comprise solar radiation.

In step 610 this, first plurality of interacted photons may be filtered. In one embodiment, this filtering may be achieved using a fixed filter, a dielectric filter, and combinations thereof. In another embodiment, this filtering may be achieved using a tunable filter. This tunable filter may be selected from the group consisting of: a liquid crystal tunable filter, a multi-conjugate tunable filter, an acousto-optical tunable filter, a Lyot liquid crystal tunable filter, an Evans split-element liquid crystal tunable filter, a Sole liquid crystal tunable filter, a ferroelectric liquid crystal tunable filter, a Fabry Perot liquid crystal tunable filter, and combinations thereof.

In one embodiment, tunable filters described herein may comprise filter technology available from ChemImage Corporation, Pittsburgh, Pa. This technology is more fully described in the following U.S. Pat. No. 6,992,809, filed on Jan. 31, 2006, entitled "Multi-Conjugate Liquid Crystal Tunable Filter," U.S. Pat. No. 7,362,489, filed on Apr. 22, 2008, entitled "Multi-Conjugate Liquid Crystal Tunable Filter," Ser. No. 13/066,428, filed on Apr. 14, 2011, entitled "Short wave infrared multi-conjugate liquid crystal tunable filter." These patents and patent applications are hereby incorporated by reference in their entireties.

In step 615 this first plurality of interacted photons may be detected to thereby generate a test data set representative of said region of interest. In one embodiment, this test data set may comprise a SWIR data set representative of said region of interest. In one embodiment, this SWIR data set may comprise at least one hyperspectral SWIR image. In another embodiment, this SWIR data set may comprise at least one of: a spatially accurate wavelength resolved SWIR image, a SWIR spectrum, and combinations thereof.

In another embodiment, this test data set may comprise a fluorescence data set representative of said region of interest. In one embodiment, this fluorescence data set may comprise at least one hyperspectral fluorescence image. In another embodiment, this fluorescence data set may comprise at least one of: a spatially accurate wavelength resolved fluoresce image, a fluorescence spectrum, and combinations thereof.

This test data set may be analyzed in step 620 to thereby identify an unknown sample within said region of interest. In one embodiment, the method 600 may further comprise providing a reference database comprising a plurality of reference data sets, each reference data set corresponding to a known sample. In one embodiment, the reference data sets may comprise at least one of: reference SWIR data sets, reference fluorescence data sets and combinations thereof. In one embodiment, the test data set may be compared to at least one reference data set using a chemometric technique. This chemometric technique may be selected from the group consisting of: principle component analysis ("PCA"), partial least squares discriminate analysis ("PLSDA"), cosine correlation analysis ("CCA"), Euclidian distance analysis ("EDA"), k-means clustering, multivariate curve resolution ("MCR"), band t. entropy method ("BTEM"), mahalanobis distance ("MD"), adaptive subspace detector ("ASD"), spectral mixture resolution, and combinations thereof. In another embodiment, pattern recognition algorithms may be used.

This unknown sample may be further interrogated in step 625 by illuminating a first portion of said unknown sample to thereby generate a second plurality of interacted photons. In one embodiment, the sample may be illuminated using a first illumination pattern. This illumination pattern may comprise at least one of: a circle, a square, a rectangle, an ellipse, an annulus, and combinations thereof.

In step 630 a second portion of said unknown sample may be illuminated to thereby generate a third plurality of interacted photons. In one embodiment, this second portion may be illuminated using a second illumination pattern. This second illumination pattern may be selected from the group consisting of: a circle, a square, a rectangle, an ellipse, an annulus, and combinations thereof.

In one embodiment, at least one of a first portion of an unknown sample and a second portion of a unknown sample may be illuminated using passive illumination, such as solar illumination. In another embodiment, at least one of a first portion of an unknown sample and a second portion of an unknown sample may be illuminated using active illumination such as a laser illumination source, a broad band light source, an ambient light source, and combinations thereof. In one embodiment this laser illumination source may comprise a tunable laser. In yet another embodiment, a combination of active and passive illumination may be implemented to illuminate a first portion of an unknown sample and a second portion of an unknown sample.

In one embodiment, a first portion and a second portion of an unknown sample may be illuminated sequentially. In another embodiment, a first portion and a second portion of an unknown sample may be illuminated simultaneously. In one embodiment a first portion of said unknown sample and a second portion of an unknown sample may be selected so as to at least partially overlap.

At least one of said second plurality of interacted photons and said third plurality of interacted photons may be filtered in step 635. In one embodiment, this filtering may be achieved using a fixed filter, a dielectric filter, and combinations thereof. In another embodiment, this filtering may be achieved using a tunable filter. This tunable filter may be selected from the group consisting of: a liquid crystal tunable filter, a multi-conjugate tunable filter, an acousto-optical tunable filter, a Lyot liquid crystal tunable filter, an Evans split-element liquid crystal tunable filter, a Sole liquid crystal tunable filter, a ferroelectric liquid crystal tunable filter, a Fabry Perot liquid crystal tunable filter, and combinations thereof.

In step 640 the second plurality of interacted photons may be detected to thereby generate a LIBS data set representative of said unknown sample. In one embodiment, this LIBS data set may comprise at least one hyperspectral LIBS image. In another embodiment, this LIBS data set may comprise at least one of: a spatially accurate wavelength resolved LIBS image, a LIBS spectrum, and combinations thereof.

In step 645 said third plurality of interacted photons may be detected to thereby generate a Raman data set representative of said unknown sample. In one embodiment, this Raman data set may comprise at least one hyperspectral Raman image representative of said unknown sample. In another embodiment, this Raman data set may comprise at least one of: a spatially accurate wavelength resolved Raman image, a Raman spectrum, and combinations thereof.

At least one of said LIBS data set and said Raman data set may be analyzed in step 650 to thereby identify said unknown sample. In one embodiment, the unknown sample may be identified as comprising at least one of: a biological material, a chemical material, an explosive material, a hazardous material, a concealment material, a non-hazardous material, and combinations thereof. Explosive materials that may be detected using the system and method disclosed herein include, but are not limited to: nitrocellulose, Ammonium nitrate ("AN"), nitroglycerin, 1,3,5-trinitroperhydro-1,3,5-triazine ("RDX"), 1,3,5,7-tetranitroperhydro-2,3,5,7-tetrazocine ("HMX") and 1,3-Dinitrato-2,2-bis(nitratomethyl) propane ("PETN").

In one embodiment, this analyzing may comprise comparing at least one of said LIBS data set and said Raman data set to at least one reference data set. This comparing maybe achieved using a chemometric technique. In one embodiment, at least one of said LIBS data set and said Raman data set may be applied to a plurality of reference data sets in a reference database, wherein each said reference data set corresponds to a known sample.

In one embodiment, analyzing said LIBS data set and said Raman data set may further comprise applying a fusion algorithm to thereby generate a fused data set. In one embodiment, this fusion may be accomplished using Bayesian fusion. In another embodiment, this fusion may be accomplished using technology available from ChemImage Corporation, Pittsburgh, Pa. This technology is more fully described in the following pending U.S. Patent Applications No. US 2009/0163369, filed on Dec. 19, 2008 entitled "Detection of Pathogenic Microorganisms Using Fused Sensor Data," Ser. No. 13/081,992, filed on Apr. 7, 2011, entitled "Detection of Pathogenic Microorganisms Using Fused Sensor Raman, SWIR and LIBS Sensor Data," US 2009/0012723, filed on Aug. 22, 2008, entitled "Adaptive Method for Outlier Detection and Spectral Library Augmentation," US 2007/0192035, filed on Jun. 9, 2006, "Forensic Integrated Search Technology," and US 2008/0300826, filed on Jan. 22, 2008, entitled "Forensic Integrated Search Technology With Instrument Weight Factor Determination." These applications are hereby incorporated by reference in their entireties. In another embodiment, the present disclosure provides for ChemFusion Improvements. Such improvements include the use of grid search methodology to establish improved weighting parameters for individual sensor modality classifiers under JFIST Bayesian architecture. In another embodiment, image weighted Bayesian fusion may be used. This fused data set may then be analyzed to identify the unknown sample.

In another embodiment, the method of the present disclosure may provide for the time-gated detection of the photons reflected, scattered, and/or plasma emitted by the sample. In such an embodiment, an illumination source may be operatively coupled to one or more detection devices so as to acquire Raman, SWIR, and/or LIBS data accordance with Raman, SWIR, and/or LIBS emission times. The use of pulsed laser excitation and time-gated detection is more fully described in U.S. patent application Ser. No. 12/802,994, filed on Jun. 17, 2010, which is hereby incorporated by reference in its entirety.

The methods of the present disclosure may further utilize telescope optics and/or zoom lenses to thereby locate and/or focus on a region of interest and/or unknown sample. The telescope optics may also be utilized to collect at least one of the plurality of interacted photons generated by illuminating at least one of a region of interest and an unknown sample.

The use of LWIR spectroscopy and imaging techniques may be used, in one embodiment, to detect human presence in a scene and human movement in a scene. This use of LWIR may be used in conjunction with motion sensing to thereby configure laser interlocking. This effectively turns off a laser when a human is present. This holds potential for increasing safety, including eye safety, of the system and method disclosed herein.

The present disclosure also provides for a system for the detection and identification of explosive and other materials. In one embodiment, a system may comprise a first illumination source configured so as to illuminate a region of internet to thereby generate a first plurality of interacted photons. In one embodiment, this first illumination source may comprise an active illumination source such as a laser illumination source, a broadband light source, an ambient light source, and combinations thereof. In one embodiment, this laser illumination source may comprise a tunable laser. In another embodiment, this first illumination source may comprise a passive illumination source such as a solar radiation source.

The system may further comprise at least one collection optics configured so as to collect said first plurality of interacted photons. This collection optics may, in one embodiment, comprise a telescope optics. A filter may be configured so as to filter the first plurality of interacted photons. This filter may comprise a tunable filter, a fixed filter, a dielectric filter, and combinations thereof. In a configuration comprising a tunable laser illumination source, a fixed filter may be implemented in the system.

A first detector may be configured so as to detect said first plurality of interacted photons and generate a test data set representative of said region of interest. In one embodiment, this detector may comprise a focal plane array detector. This focal plane array detector may comprise at least one of: an InGaAs detector, a CMOS detector, an ICCD detector, a CCD detector, and combinations thereof. In one embodiment, this first detector may be configured so as to generate a SWIR test data set representative of said region of interest. In another embodiment, this first detector may be configured so as to generate a fluorescence test data set representative of said region of interest.

A means for analyzing said test data may include software configured so as to compare the test data set to reference data sets in a reference library. This comparing may be achieved by applying a chemometric technique. This analysis may target an unknown material in the region of interest.

A second illumination source may be configured so as to illuminate at least a portion of the unknown material to thereby generate a second plurality of interacted photons. This second illumination source may comprise at least one of: a passive illumination source, a laser illumination source, a broadband light source, an ambient light source, and combinations thereof. A second detector may be configured so as to detect this second plurality of interacted photons and generate a LIBS data set representative of the unknown material. A third illumination source may be configured to illuminate a second portion of the unknown sample to thereby generate a third plurality of interacted photons. This second illumination source may comprise at least one of: a passive illumination source, a laser illumination source, a broadband light source, an ambient light source, and combinations thereof. A third detector may be configured so as to detect the third plurality of interacted photon and generate a Raman data set representative, of said unknown material.

In one embodiment, at least one of a second detector and a third detector may comprise at least one focal plane array detector. This focal plane array detector may comprise at least one of: an InGaAs detector, a CMOS detector, an ICCD detector, a CCD detector, and combinations thereof.

The system may further comprise a means for analyzing at least one of said LIBS data set and said Raman data set to thereby identify said unknown material. This means may comprise software configured to compare at least one of the LIBS data set and the Raman data set to a reference data set. This may be achieved by applying at least one chemometric technique. This may also be achieved by applying a fusion algorithm.

Figure 7:
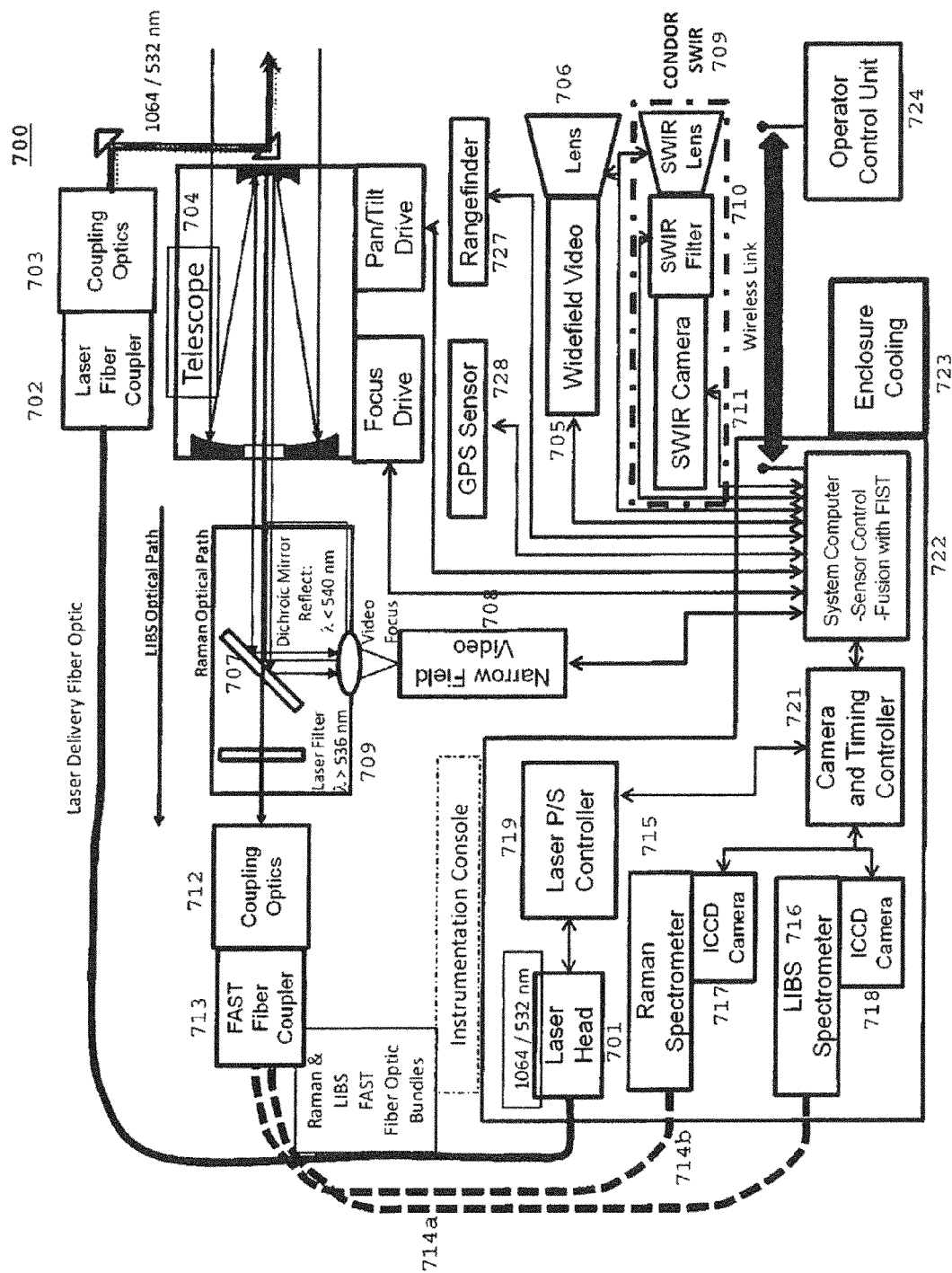
FIG. 7 is illustrative of a system of the present disclosure.

In one embodiment, the system of the present disclosure may incorporate CONDOR-ST technology available from ChemImage Corporation, Pittsburgh, Pa. One embodiment of a system of the present disclosure is illustrated in FIG. 7. In one embodiment, the system 700 may comprise a first optical system optically coupled to an illumination source, which is illustrated in FIG. 7 as laser head 701. In addition to laser head 701 the system may utilize at least one of: a broadband light source and an ambient tight source. In one embodiment, the laser head 710 may be coupled to a laser controller 719 for configuring the laser. In some embodiments, it may not be required for the illumination source to be physically coupled to the system 700, for example when an ambient light source such as the sun is used as an illumination source. The first optical system may comprise a laser fiber coupler 702, a coupling optics 703, and a telescope 704.

In one embodiment, the components of the first optical system are matched to one or more mirrors of the telescope, and expand the laser beam to fill the mirror. The laser excitation pulse may propagate along the telescope's optical axis and present a laser spot that dills the telescope's field of view at the chosen focal point. This allows for a 180 degree backscattering collection geometry and enables repositioning and refocusing of the telescope 704 and laser spot simultaneously.

The system 700 may further comprise a visible imaging device, which is illustrated in FIG. 7 as a video capture device 705. The video capture device 705 may be configured to output a dynamic image of the region of interest and/or target area in real time. This video capture device 705 may be configured to operate in a targeting mode in which it surveys a region of interest/target area. Video is highly sensitive but may have a low specificity, in that it provides for a low level means of classifying objects based on morphological factors such a size, shape, and color. Such first-order discrimination may provide good guidance for higher order classification and detection such as Raman, SWIR, and/or LIBS spectroscopy and imaging. In one embodiment, the video capture device 705 may utilize a target scope to provide for a large area of view and zoom control. In one embodiment, this target scope may be incorporated into the lens 706 associated with the video capture device 705. The system 700 may further comprise a narrow field video device 720 for obtaining additional video data.

The video capture device 705 may use ambient light or light from laser light source 701 to illuminate the target area. The video capture device 705 may also collect a series of small images, that are recombined into a larger, macro-image for analysis. The video capture device 705 operates in the first order targeting mode to rapidly screen objects based on the intrinsic size, shape and color properties of the particles. Regions of interest suspected to possess explosive residues are located and identified, honing in on the target area at which to conduct further analysis using LIBS/Raman imaging spectroscopy that provide greater specificity.

The system 700 may also comprise a second optical system that collects at least one of photons reflected, scattered, and/or plasma emitted by a region of interest and/or target area. This second optical system may direct the collected reflected photons to a first two-dimensional array of detection elements for SWIR spectroscopic analysis. This second optical system may direct the collected scattered and/or plasma emitted photons to a fiber array spectral translator device. The second optical system may comprise a telescope 704, a mirror 703, a filter 709, and a coupling optics 712. In one embodiment, the system may further comprise a dichroic beam splitter. In one embodiment, this dichroic beam splitter may enable simultaneous Raman acquisition and visual targeting.

Alternatively, a lens 709 can collect reflected photons from a region of interest and/or target area and direct the reflected photons to a SWIR filter 710 which may comprise at least one of a SWIR liquid crystal tunable and SWIR multi-conjugate liquid crystal tunable filter. The SWIR filter 710 may effectively filter a plurality of reflected photons into a plurality of wavelength bands. The wavelength bands include wavelengths characteristic of the sample undergoing analysis. The wavelengths that can be passed through a tunable filter may range from 200 nm (ultraviolet) to 2000 nm (far infrared). The choice of a tunable filter depends on the desired optical region and/or the nature of the sample being analyzed. The reflected photons may then be detected at a SWIR detector, shown in FIG. 7 as a SWIR camera 711. The SWIR camera 711 may be configured to output a dynamic image of the region of interest/target area. The SWIR camera 711 may also be configured to output at least one of: a SWIR hyperspectral image, a plurality of spatially resolved SWIR spectra, and a plurality of spatially resolved SWIR images. The SWIR camera 711 may be configured to operate in real-time. The lens 709 may be configured to be operatively coupled to telescope optics to thereby increase the magnification and sensitivity of SWIR detection. Telescope optics may also be used to increase illumination NA to decrease NOHD.

The second optical system's coupling optics 712 may be operatively coupled to fiber array spectral translator device comprising a fiber array spectral translator device fiber coupler 717 and fiber array spectral translator fiber optic bundles 714a and 714b. One end of said fiber optic bundles 714a and 714b is operatively connected to at least one spectrometer. In FIG. 7, fiber optic bundles 714a and 714h are operatively connected to one of a Raman spectrometer 715 and a LIBS spectrometer 716. In another embodiment, a Raman grating array and a LIBS grating array may be incorporated into a single spectrometer.

A Raman spectrometer 715 may disperse said scattered photons output by said fiber array spectral translator device to generate a plurality of spatially resolved Raman spectra. A Raman detector 717 may detect the spatially resolved Raman spectra. A LIBS spectrometer 716 may disperse said plasma emitted photons output by said fiber array spectral translator device to generate a plurality of spatially resolved atomic spectra. A LIBS detector may detect the spatially resolved atomic spectra.

The system 700 may also comprise a pan/tilt drive unit 726 and a focus drive unit 725 to control the operation of elements of the system 700. The system 700 may further comprise a range finer 727 and a GPS sensor 728 for finding, locating, and/or targeting. The system 700 may further comprise an operator control unit 724 for interfacing with a user and allowing the user to operate the system 700.

The system 700 may also comprise a cooling enclosure 727, a camera and timing controller coupled to one or more detectors 717 and 718, and a system computer 722. The system computer 722 may be configured to perform fusion and to control the system 700.

In another embodiment, the present disclosure provides for a storage medium containing machine readable program code, which, when executed by a processor, causes said processor to perform the methods of the present disclosure. In one embodiment, processor may perform the following: illuminating a region of interest to thereby generate a first plurality of interacted photons; filtering said first plurality of interacted photons; detecting said first plurality of interacted photons to thereby generate a test data set representative of said region of interest; analyzing said test data set to thereby identify a unknown sample within said region of interest; illuminating a first portion of said unknown sample to thereby generate a second plurality of interacted photons; illuminating a second portion of said unknown sample to thereby generate a third plurality of interacted photons; filtering at least one of said second plurality of interacted photons and said third plurality of interacted photons; detecting said second plurality of interacted photons to thereby generate a LIBS data set representative of said unknown sample; detecting said third plurality of interacted photons to thereby generate a Raman data set representative of said unknown sample; and analyzing at least one of said LIBS data set and said Raman data set to thereby identify said unknown sample.

In one embodiment, the storage medium, wherein said machine readable program code, when executed by said processor, causes said processor to further compare at least one of said LIBS data set and said Raman data set to at least one reference data set associated with a known material.

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

What is claimed is:

1. A system comprising:
    a first illumination source configured to illuminate a region of interest to thereby generate a first plurality of interacted photons;
    a first detector configured so as to detect said first plurality of interacted photons and generate a test data set representative of said region of interest;
    a means for analyzing said test data set and identifying a unknown sample within said region of interest;
    a second illumination source configured so as to illuminate a first portion of said unknown sample to thereby generate a second plurality of interacted photons;
    a second detector configured so as to detect said second plurality of interacted photons and generate a LIBS data set representative of said unknown sample;
    a third illumination source configured so as to illuminate a second portion of said unknown sample to thereby generate a third plurality of interacted photons;
    a third detector configured so as to detect said third plurality of interacted photons and generate Raman data set representative of said sample; and a means for fusing said LIBS data set and said Raman data set to generate a fused data set and analyzing the fused data set to thereby identify said unknown sample.

2. The system of claim 1 further comprising at least one filter selected from the group consisting of: a tunable filter, a fixed filter, a dielectric filter, and combinations thereof, wherein said filter is configured so as to filter at least one of said first plurality of interacted photons, said second plurality of interacted photons, said third plurality of interacted photons, and combinations thereof.

3. The system of claim 2 wherein said filter comprises a tunable filter selected from the group consisting of: a liquid crystal tunable filter, a multi-conjugate tunable filter, an acousto-optical tunable filter, a Lyot liquid crystal tunable filter, an Evans split-element liquid crystal tunable filter, a Sole liquid crystal tunable filter, a ferroelectric liquid crystal tunable filter, a Fabry Perot liquid crystal tunable filter, and combinations thereof.

4. The system of claim 1 further comprising a fiber array spectral translator device for passing at least one of said first plurality of interacted photons to said first detector, said second plurality of interacted photons to said second detector, said third plurality of interacted photons to said third detector, and combinations thereof.

5. The system of claim 1 wherein said first detector is configured so as to generate said test data set, wherein said test data set comprises at least one of a SWIR data set, a fluorescence data set, and combinations thereof.

6. The. system of claim 1 wherein at least one of said first detector, said second detector, said third detector, and combinations thereof comprise a focal plane array detector.

7. The system of claim 6 wherein said focal plane array detector is selected from the group consisting of: an InGaAs detector, a CMOS detector, an ICCD detector, a CCD detector, and combinations thereof.

8. The system of claim 1 further comprising a reference database comprising a plurality of reference data sets, each reference data set corresponding to a known unknown sample.

9. The system of claim 8 wherein said plurality of reference data sets comprise at least one of: a Raman reference data set, a LIBS reference data set, a fluorescence reference data set, a SWIR reference data set, and combinations thereof.

10. The system of claim 8 further comprising a means for comparing at least one of said test data set and said fused data set to said plurality of reference data sets.

11. The system of claim 1 wherein said first illumination source comprises at least one of: a passive illumination source, a laser light source, a broadband light source, an ambient light source, and combinations thereof.

12. The system of claim 1 wherein at least one of said second illumination source and said third illumination source comprise at least one of: a passive illumination source, a laser light source, a broadband light source, an ambient light source, and combinations thereof.

13. The system of claim 1 wherein said means for analyzing said fused data set is configured so as to identify said unknown sample as at least one of: a biological material, a chemical material, an explosive material, a hazardous material, a concealment material, a non-hazardous material, and combinations thereof.

14. The system of claim 1 further comprising at least one telescope optics for collecting at least one of said first plurality of interacted photons, said second plurality of interacted photons, said third plurality of interacted photons, and combinations thereof.

15. The system of claim 1 further comprising at least one zoom lens.

16. A storage medium containing machine readable program code, which, when executed by a processor, causes said processor to perform the following:
    illuminate a region of interest to thereby generate a first plurality of interacted photons;
    filter said first plurality of interacted photons;
    detect said first plurality of interacted photons to thereby generate a test data set representative of said region of interest;
    analyze said test data set to thereby identify a unknown sample within said region of interest;
    illuminate a first portion of said unknown sample to thereby generate a second plurality of interacted photons;
    illuminate a second portion of said unknown sample to thereby generate a third plurality of interacted photons;
    filter at least one of said second plurality of interacted photons and said third plurality of interacted photons;
    detect said second plurality of interacted photons to thereby generate a LIBS data set representative of said unknown sample;
    detect said third plurality of interacted photons to thereby generate a Raman data set representative of said unknown sample;
    fuse said LIBS data set and said Raman data set to generate a fused data set; and
    analyze the fused data set to thereby identify said unknown sample.

17. The storage medium of claim 16, wherein said machine readable program code, when executed by said processor, causes said processor to further perform the following: Compare said fused data set to at least one reference data set associated with a known material.

* * * * *